United States Patent
Kempa et al.

(10) Patent No.: US 10,082,499 B2
(45) Date of Patent: Sep. 25, 2018

(54) SHORT TERM ISOTOPE PULSE LABELING METHOD FOR ANALYSING METABOLIC PRODUCTS IN BIOLOGICAL SAMPLES

(71) Applicant: Max-Delbrueck-Centrum fuer Molekulare Medizin, Berlin (DE)

(72) Inventors: Stefan Kempa, Berlin (DE); Matthias Pietzke, Berlin (DE); Christin Zasada, Berlin (DE)

(73) Assignee: MAX-DELBRUECK-CENTRUM FUER MOLEKULARE MEDIZIN, Berlin (DE)

( * ) Notice: Subject to any disclaimer, the term of this patent is extended or adjusted under 35 U.S.C. 154(b) by 180 days.

(21) Appl. No.: 14/712,357

(22) Filed: May 14, 2015

(65) Prior Publication Data

US 2015/0330969 A1    Nov. 19, 2015

(30) Foreign Application Priority Data

May 14, 2014    (EP) .................................... 14168322

(51) Int. Cl.
| | |
|---|---|
| *G01N 33/50* | (2006.01) |
| *C12Q 1/04* | (2006.01) |
| *G01N 33/58* | (2006.01) |
| *H01J 49/00* | (2006.01) |
| *G01N 33/68* | (2006.01) |

(52) U.S. Cl.
CPC ........... *G01N 33/5038* (2013.01); *C12Q 1/04* (2013.01); *G01N 33/58* (2013.01); *G01N 33/6848* (2013.01); *H01J 49/0036* (2013.01); *G01N 2458/15* (2013.01); *G01N 2570/00* (2013.01)

(58) Field of Classification Search
None
See application file for complete search history.

(56) References Cited

U.S. PATENT DOCUMENTS

| | | | |
|---|---|---|---|
| 2006/0263296 A1* | 11/2006 | Kinniburgh ........ | A61K 51/0491 424/9.1 |
| 2010/0278829 A1* | 11/2010 | Edwards, III .... | C07K 14/70596 424/136.1 |
| 2014/0134231 A1* | 5/2014 | Perera .................. | C12Q 1/6886 424/450 |

FOREIGN PATENT DOCUMENTS

WO    2005051434 A1    6/2005

OTHER PUBLICATIONS

Koek, Maud M., et al.: "Quantitative metabolomics based on gas chromatography mass spectrometry: status and perspectives", published Nov. 16, 2010.
Pietzke, Matthias et al.: "Decoding the dynamics of cellular metabolism and the action of 3-bromopyruvate and 2-deoxyglucose using pulsed stable isotope-resolved metabolomics", published Jun. 30, 2014.
Pietzke, Matthias et al.: "Pulsed Stable Isotope-Resolved Metabolomic Studies of Cancer Cells", published in 2014.
European Search Report form EP Application No. 14168322 dated Nov. 25, 2014.
Le You et al: "Application of Stable Isotope-Assisted Metabolomics for Cell Metabolism Studies", Metabolites, vol. 4, No. 2, Mar. 31, 2014 (Mar. 31, 2014), pp. 142-165.
Moseley Hunter NB: "Correcting for the effects of natural abundance in stable isotope resolved metabolomics experiments involving ultra-high resolution mass spectrometry", BMC Bioinformatics, Biomed Central, London, GB, vol. 11, No. 1, Mar. 17, 2010 (Mar. 17, 2010), p. 139.

* cited by examiner

*Primary Examiner* — Leon B Lankford, Jr.
(74) *Attorney, Agent, or Firm* — Fox Rothschild LLP

(57) ABSTRACT

The present invention relates to a method for preparation of labeled metabolic products, comprising the steps (a) providing a biological sample in vitro, (b) contacting the biological sample with a labeling buffer comprising a labeled substrate, wherein the substrate comprises at least one carbon atom and represents an educt or intermediate of a metabolic process of the biological sample and wherein the label is a stable isotope, (c) washing the biological sample using a wash-buffer, wherein said wash-buffer comprises a carbon resource such that the biological sample is precluded from carbon deficiency during said washing, wherein said carbon resource comprises the substrate according to step b), wherein said substrate in the wash-buffer may be labeled or unlabeled, (d) quenching the biological sample such that metabolic processes within the biological sample are slowed down or stopped and (e) extracting the labeled metabolic product from the biological sample. The present invention further refers to methods for quantification of labeled metabolic products from biological sample.

15 Claims, 12 Drawing Sheets

Figure 1:
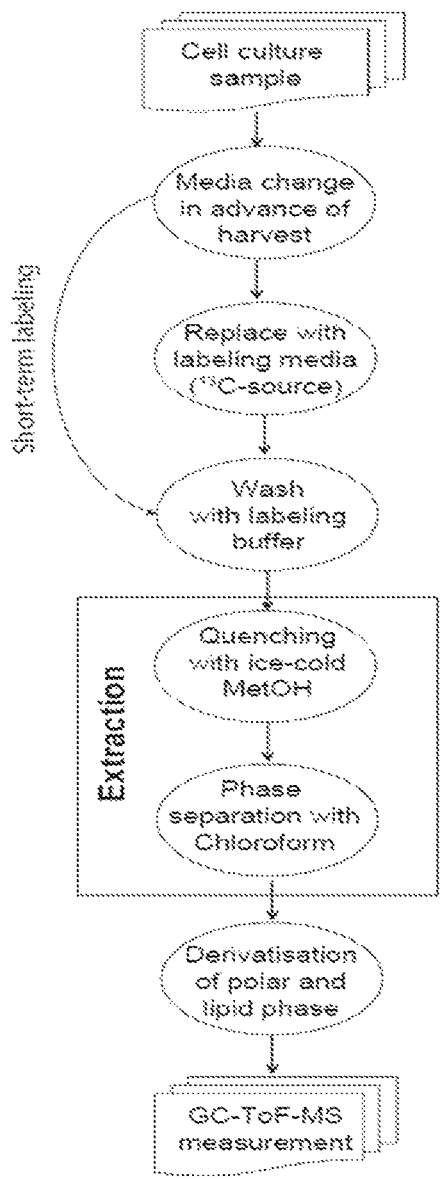
Figure 1:
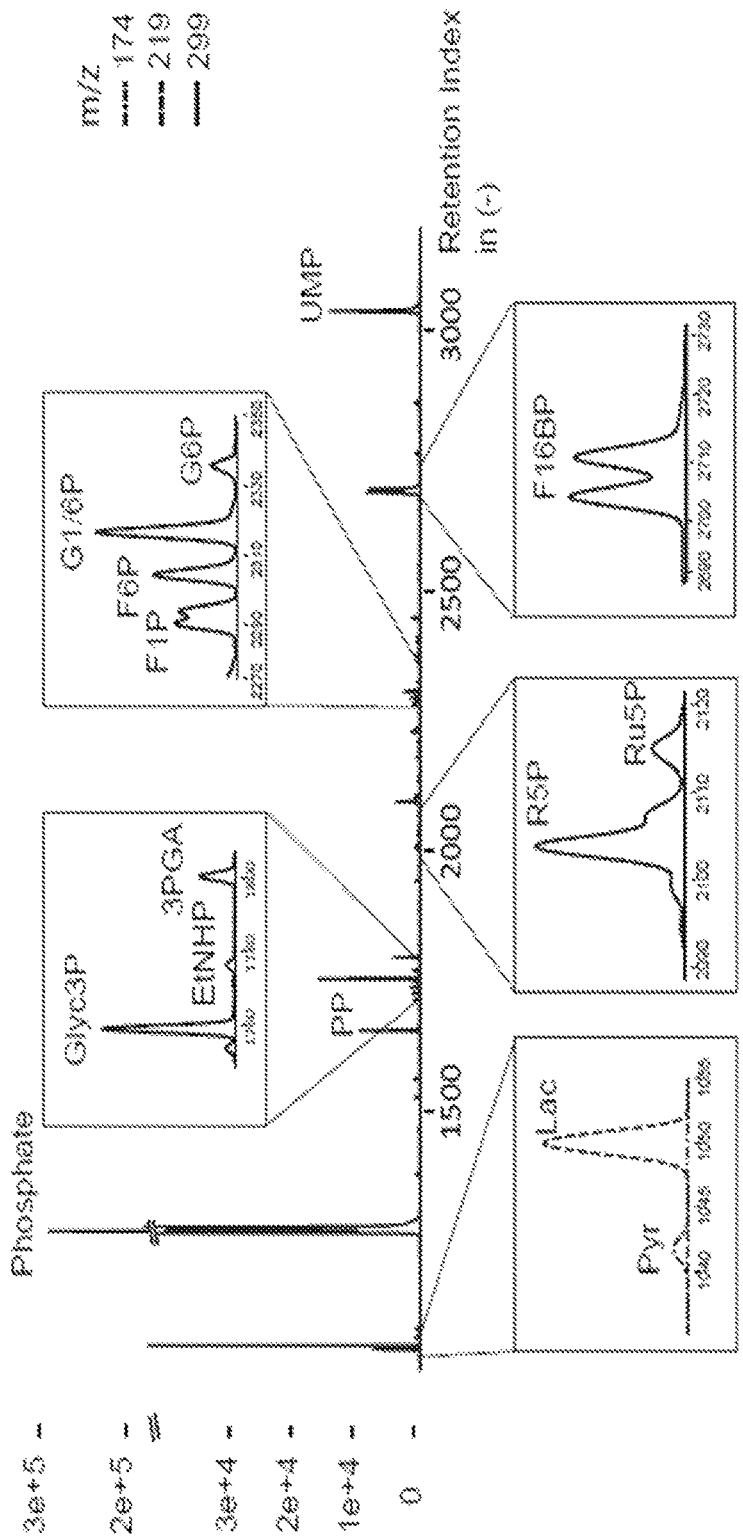

SHORT TERM ISOTOPE PULSE LABELING METHOD FOR ANALYSING METABOLIC PRODUCTS IN BIOLOGICAL SAMPLES

CROSS-REFERENCE TO RELATED APPLICATION

This application claims priority to and the benefit of European Application No. 14168322.7, filed May 14, 2014, the entirety of which is hereby incorporated herein by reference.

Central metabolism is highly dynamic and continuously adjusted to the physiological program of the cell, organ and organism. In a healthy state cellular metabolism is tightly regulated to guarantee physiological function and the efficient usage of available resources. However, the underlying mechanisms leading to metabolic dysfunction are often poorly understood.

Metabolic flux is an expression of the activity of a network of enzymatic reactions. This network is influenced by several factors; the expression levels of the catalytic enzymes, but also strongly by the relative concentrations of substrates and products. In addition, allosteric regulation and post-translation modifications, including phosphorylation, ubiquitylation and acetylation control metabolic activity. As such, metabolic flux cannot be inferred from transcript or indeed protein levels of constituent enzymes but rather requires direct determination. Several techniques for metabolic flux analysis have been established previously. Some methods rely on the quantification of substrate usage and metabolic products of the cellular system over time. Integration of further parameters, such as cell growth and biomass production provide an overall quantification of metabolic efficiency and performance. However, such methods do not allow a distinct view of individual pathways and discrete fluxes.

In order to achieve a positional map of metabolic activity the fate of metabolic substrates within the network has to be resolved. In the early days of biochemistry radioactive isotopes were used to identify the structure of the most important metabolic pathways glycolysis, the TCA cycle, the Calvin-Benson cycles. Nowadays, the use of stable isotopes (e.g. carbon-13 or nitrogen-15) in combination with mass spectrometry or nuclear magnetic resonance allows a detailed analysis of metabolism. Typically, stable isotopes labeled substrates are fed to cells, producing an individual positional isotope pattern in the metabolic intermediates.

The determination of such patterns increases the knowledge about metabolic activity and substrate routing within the cellular system. Such studies have already revealed new insights into the regulation of the central metabolism by well characterized oncogenes. However, the long labeling times used to date enable a qualitative description of the metabolic activity rather determining the rates of individual enzymatic reactions or short termed changes within metabolism. Hence, new methods that allow for direct measurement of dynamic metabolic activity over the central metabolic pathways are needed.

The present invention relates to methods enabling the time-resolved, quantitative analysis of the metabolism using stable isotopes and mass spectrometry. Specifically, the present invention relates to a pulse labeling method (pSIRM, pulsed stable isotope resolved metabolomics).

Surprisingly, it has been found that an optimized method for preparation of labeled metabolic products that does not disturb cellular metabolism by precluding the cells from nutritional deficiencies as well as a novel quantification method for labeled metabolic products allows the determination of absolute quantities of metabolic products especially with a high coverage of metabolic intermediates and the determination of stable isotope incorporation into metabolic products.

According to the present invention, a method for preparation of labeled metabolic products is provided aiming at preserving the metabolic homeostasis during the preparation process. This means that during the whole preparation process a continuous supply of major nutrients is ensured which prevents the disruption of cellular metabolism.

The present invention is directed to a method for preparation of labeled metabolic products, comprising the steps: (a) providing a biological sample in vitro; (b) contacting the biological sample with a labeling buffer comprising a labeled substrate, wherein the substrate comprises at least one carbon atom and represents an educt or intermediate of a metabolic process of the biological sample and wherein the label is a stable isotope; (c) washing the biological sample using a wash-buffer, wherein said wash-buffer comprises a carbon resource such that the biological sample is precluded from carbon deficiency during said washing, wherein said carbon resource comprises or consists of the substrate according to step b), wherein said substrate in the wash-buffer may be labeled or unlabeled; (d) quenching the biological sample such that metabolic processes within the biological sample are slowed down or stopped; and (e) extracting the labeled metabolic product from the biological sample.

After step b) where the biological sample is contacted with a labeling buffer comprising a labeled substrate, preferably the labeling buffer is removed from the biological sample before the biological sample is washed with a wash-buffer according to step c).

In the present invention, the term "labeled" or "label" is intended to mean any kind of tag that marks a target, which can be a labeled substrate or one or more labeled metabolic products. The label can be an isotope. Preferably, the label is a stable isotope which means that it is a non-radioactive isotope. Stable isotopes of elements are isotopes having identical numbers of protons and electrons, but having an additional neutron which increases the molecular weight of the element by one mass unit. Preferably, the stable isotopes $^{13}C$, $^{2}H$, $^{15}N$, $^{18}O$ and $^{34}S$ are used.

A "substrate" can be any substance suitable to be labeled with e.g. a stable isotope. The substrate comprises at least one carbon atom and represents an educt or intermediate of a metabolic process of the biological sample. According to the present invention, the labeled substrate is a peptide, an amino acid, a carbohydrate, a lipid, a fatty acid or pyruvate. Preferred amino acids are glutamine, arginine, leucine, lysine, methionine, phenylalanine, threonine, and tyrosine. More preferably glutamine is used. Suitable lipids are e.g. fatty acids and their derivatives (including tri-, di-, monoglycerides and phospholipids), triglycerides and isoprenoids (e.g. cholesterol). Preferably, the labeled substrate is a carbohydrate, more preferably a sugar such as fructose, galactose, glucose, lactose, mannose, ribose or triose. More preferably glucose is used.

As used herein the term "metabolic products" denotes any substance produced by metabolism or by a metabolic process of a cell, a tissue or an organism such as metabolic intermediates or metabolic end products. Metabolic products can be obtained from e.g. conditioned media, cell culture supernatants, extracts from biological samples or extracts from body fluids.

The labeled metabolic product referred to in the present invention is preferably a carbohydrate, (poly) peptide, lipid, fatty acid, nucleic acid, or a metabolite. Metabolites are small molecule compounds which are preferably understood as molecules having a mass <1 kDa.

Metabolic pathways are well known in the art and may vary between species. Preferably, said pathways include at least citric acid cycle, respiratory chain, photosynthesis, photorespiration, glycolysis, gluconeogenesis, hexose monophosphate pathway, oxidative pentose phosphate pathway, synthesis and β-oxidation of fatty acids, urea cycle, amino acid biosynthesis pathways, protein biosynthesis pathways and protein degradation pathways such as proteasomal degradation, amino acid degrading pathways, biosynthesis or degradation of: lipids, peptides, polyketides (including e.g. flavonoids and isoflavonoids), isoprenoids (including e.g. terpenes, sterols, steroids, carotenoids, xanthophylls), carbohydrates, phenylpropanoids and derivatives, alkaloids, benzenoids, indoles, indole-sulfurcompounds, porphyrines, anthocyans, hormones, vitamins, cofactors such as prosthetic groups or electron carriers, lignin, glucosinolates, purines, pyrimidines, nucleosides, nucleotides and related molecules such as tRNAs, microRNAs (miRNA) or mRNAs.

Accordingly, small molecule compound metabolites are preferably composed of the following classes of compounds: alcohols, alkanes, alkenes, alkines, aromatic compounds, ketones, aldehydes, carboxylic acids, esters, amines, imines, amides, cyanides, amino acids, peptides, thiols, thioesters, phosphate esters, sulfate esters, thioethers, sulfoxides, ethers, or combinations or derivatives of the aforementioned compounds. The small molecules among the metabolites may be primary metabolites which are required for normal cell or organ function and growth, development or health. Moreover, small molecule metabolites further comprise secondary metabolites which e.g. allow an organism to adapt to its environment or play an important role in interspecies defenses like e.g. toxins.

A "biological sample" as used herein may comprise, be derived from or consist of biological material like e.g. cells, tissue or fluid derived from a biological source or of constituents which have been derived therefrom. Preferably, the biological sample is a cell or tissue sample. A cell sample e.g. refers to any prokaryotic cell (e.g. bacterial cell) or eukaryotic cell (yeast cell, plant cell, animal cell, mammalian cell, etc.). Optionally, the biological sample may be pretreated, e.g. by pre-incubation with certain pharmacological substances, prior to the sample preparation method.

According to the present invention, the biological sample is a sample that is used in an in vitro method. "In vitro" means any environment, which is not located within a living organism such as a human or animal body. Thus, the in vitro method of the invention explicitly does not comprise a method which is practiced on the human or animal body.

Prior step b) of the preparation method of the present invention where the biological sample is contacted with a labeling buffer comprising a labeled substrate, it is preferred to change the culture medium of the biological sample to minimize concentration changes of nutrients during stable isotope labeling. Preferably, the culture medium is changed 0.5 to 24 hours, more preferably 1 to 10 hours, even more preferred 2 to 4 hours prior contacting the biological sample with a labeling buffer comprising a labeled substrate.

During step b) of the preparation method of the present invention, the biological sample is contacted with a labeling buffer comprising a labeled substrate. The term "contacting" or "contacted" means a physical state of touching and is performed under conditions which allow the respective metabolic pathway to function. Suitable conditions under which the biological sample can be contacted are known in the art. These conditions preferably include a liquid medium and/or contacting at a temperature of >0° C. to <60° C. The contacting is carried out for a sufficient period of time which allows the incorporation of the labeled isotope into the metabolic product. Preferably, the period of time wherein the biological sample is contacted with the labeling buffer is <15 min, more preferably 0.1 to 10 min, even more preferred 0.5 to 8 min, mostly preferred 1 to 5 min.

The labeling buffer comprises the labeled substrate and provides an aqueous environment suitable to effectively contact the biological sample with the labeled substrate. For this purpose, the labeling buffer may comprise further components, additives and salts in addition to the labeled substrate. The labeling buffer is suited to allow the metabolic process of the biological sample to be studied to function. The exact nature and composition of said labeling buffer depends on the biologic sample used and the metabolic process to be studied. The skilled person is well aware of suitable labeling buffers for use. The labeling buffer used for contacting the biological sample may comprise some or all essential nutrient resources for the biologic sample wherein the labeled substrate may represent one of said nutrient resources. The labeling buffer may be designed to comprise only the resources and constituents that are minimally required to allow the metabolic process of the biological sample to be studied to function. However, the labeling buffer may also comprise further nutrients, additives, salts and components. The labeling buffer may be a full medium. For pSIRM experiments with incubation times longer than 5 minutes it is preferred to use full medium as labeling buffer.

After contacting the biological sample with a labeling buffer comprising a labeled substrate (step b), the biological sample is washed with a wash-buffer (step c) in order to remove undesired constituents of the labeling buffer that may influence further preparation steps or negatively affect quantification of the labeled metabolic products. Furthermore, due to the removal of the labeling buffer from the biological sample and the following washing step, it is possible to differentiate between extra- and intracellular metabolic products when analysing metabolic processes in biological samples. Metabolic processes of a biological sample are fast and highly regulated processes. During the washing step, the metabolism of the biological sample proceeds and the production of metabolic products continues. However, the wash-buffer in labeling experiments known in the art does usually not comprise any nutrient resources, such that the biological sample suffers from a nutrient shortage during said washing. This nutrient shortage rapidly induces adapting mechanisms of the biological sample and also affects the metabolic products that are subsequently produced. Hence, experimental procedures known in the art lead to metabolic products that do not reflect the physiological metabolic state when nutrients are continuously present. This problem is solved according to the invention by providing the biological sample with the relevant resources also during the wash steps.

According to the present invention, nutrient resources such as nitrogen, sulphur or carbon resources are added to the wash-buffer to avoid nutrient deficiencies during the preparation of the metabolic products from the biological sample. In particular, the wash-buffer comprises a carbon resource such that the biological sample is precluded from carbon deficiency during said washing. "Carbon deficiency" means a lack or shortage of carbon as a nutrient source. The carbon resource within the wash-buffer comprises the substrate used in the contacting step b) wherein said substrate in the wash-buffer may be labeled or unlabeled. Preferably, the carbon source within the wash-buffer is a carbohydrate, mono- or polyvalent alcohol, fatty acid, amino acid or pyruvate and/or combinations thereof. Carbohydrates, also called saccharides, are divided into four chemical groups: polysaccharides (e.g. starch), oligosaccharides (e.g. raffinose), disaccharides and monosaccharides. Preferably, mono- and disaccharides such as glucose, fructose, saccharose, dextrose, lactose and/or combinations thereof are used. Preferred mono- or polyvalent alcohols are glycerin, mannitol, isomalt, lactitol, sorbitol, glucitole, xylitol, threit, erythritol, arabite and/or combinations thereof. Preferred amino acids are glutamine, arginine, cysteine, glycine, histidine, leucine, methionine, phenylalanine, serine, threonine, tryptophan, tyrosine and valine, more preferably, glutamine is used. The wash-buffer may comprise further constituents, additives and salts to maintain osmolality and pH.

The biological sample is washed with the wash-buffer for a sufficient period of time which allows the removal of extracellular metabolic products from the biological sample. Preferably, the period of time is <10 min, more preferably 0.1 to 5 min, even more preferred 0.2 to 2 min. The washing step may be performed one or more times.

After the washing step c), the biological sample is quenched. "Quenching" or "quenched" means that metabolic processes within the biological sample are slowed down or stopped. Quenching can be achieved e.g. by cold or hot treatment or lysis of the biological sample. Preferably, the biological sample is quenched by cold treatment. "Cold treatment" means rapidly decreasing the culture temperature to values below 0° C. This can be achieved by methods well known in the art e.g. by using aqueous alcohol solutions at temperatures of −5° C. to −50° C., preferably −10° C. to −40° C., more preferred −20° C. to −30° C. Also, liquid nitrogen may be used. Preferably, MeOH/$H_2O$ is used.

After quenching the metabolic products are extracted using methods well known in the art. The term "extraction" means to separate, to isolate or to free the metabolic products from other constituents of the biological sample. Extraction may imply separation of parts from the biological sample or purification of the metabolic products. Suitable extraction methods are known in the art and have been described e.g. in the articles "Deregulated MYC expression induces dependence upon AMPK-related kinase 5" (Liu et al., Nature 2012) or "Synthetic lethal metabolic targeting of cellular senescence in cancer therapy" (Dörr et al., Nature 2013).

The present invention is also directed to a method for quantification of a labeled metabolic product from a biological sample as well as determination of the degree of stable isotope incorporation using the concept of mass isotopomer analysis. This analysis relies on the information about the incorporation of heavy carbon atoms in the metabolic products, which is inherited within the intensity shift between isotopomers in the mass spectra. Hence, for a reliable analysis of isotopomers corresponding mass spectra data are required.

A mass spectrum of a given chemical compound can be represented as an intensity vs. mass-to-charge ratio (m/z) plot. Mass spectra can be acquired using different methods. Preferably, the mass spectra of the test and reference sample are determined using mass spectrometry (MS), electron impact ionization (EI), electro spray ionization (ESI), atmospheric pressure chemical ionization (APCI), nuclear magnetic resonance spectroscopy (NMR), liquid chromatography (LC), gas chromatography (GC) or capillary electrophoresis (CE) and/or combinations thereof. More preferably, gas chromatography-mass spectrometry (GC-MS) is used.

Not all mass spectra of a given substance are the same: some mass spectrometers detect the intact molecular masses with little fragmentation others break the analyte molecules into fragments and measure the masses of the fragments. For example, electron impact ionisation (EI) gives a high degree of fragmentation, yielding highly detailed mass spectra and can provide important information for structural elucidation or characterization and facilitates the identification of unknown compounds. This harsh ionization allows even monitoring of uncharged molecules, such as alkanes, and suffers less from ion suppression. Electron impact ionisation is the standard ionization technique used for gas chromatography coupled to mass spectrometry (GC-MS).

Mass spectra usually are presented as histograms. The x-axis of a mass spectrum represents a relationship between the mass of a given fragment and the number of elementary charges that it carries (m/z). The y-axis of a mass spectrum represents signal intensity of the charges represented as peaks ("peak intensities"). In most forms of mass spectrometry, the intensity of ion current measured by the spectrometer approximately correlates with the relative abundance of the ion. In order to get more quantitative information out of a mass spectrum it is common to create a standard curve to compare the sample to.

According to the present invention, a data analysis workflow has been established in order to determine stable isotope incorporation into metabolic products. With this approach the quantity of a compound and the degree of stable isotope incorporation can be determined from the peak intensities and distribution of the mass isotopomers within the same measurement.

To analyse the quantitative mass isotopomer distribution of the corresponding fragments, peak lists including the mass-spectral information were generated. Mass isotopomer fractions (MIF) are calculated based on the extracted peak intensities within substance-specific defined mass ranges. The term "mass isotopomer fractions" or "MIF" is the abundance of a group of mass isotopomers, which means isotopomers with the same m/z-ratio, within the whole mass range of possible isotopologues of a compound, meaning all naturally and artificially enriched isotopes. MIF is the percentage value of an isotope mass fragment. If substances are present in different concentrations, it is difficult to compare them. This can be normalized by calculating MIF. Summing up the MIFs of the whole mass range, i.e. ("M+0"+"M+1"+ . . . +"M+n") makes in total 100%.

Mathematical approaches to calculate stable isotope incorporation are already included into existing software packages. Usually these approaches require the complete knowledge of the chemical composition of the analysed mass fragment. According to the present invention, a method to calculate stable isotope incorporation by subtracting natural occurring stable isotope abundances from experimentally derived mass spectra has been established which does not require prior knowledge of the chemical composition of the mass fragments and facilitates the analysis of stable isotope incorporation into unknown compounds.

The present invention is directed to a method for quantification of a labeled metabolic product from a biological sample, comprising the steps: (a) providing a test sample comprising a labeled metabolic product; (b) providing a reference sample comprising unlabeled metabolic product; (c) determining mass spectra of the test sample of step a) and of the reference sample of step b); (d) calculating corresponding mass isotopomer fractions (MIF) for test and reference sample based on respective peak intensities or peak areas extracted from mass spectra of step c) preferably according to Formula (0);

$$MIF_x = \frac{Intensity_x}{\sum_{x=m0}^{x=m+n} Intensity_x} * 100\% \quad (0)$$

wherein $MIF_x$=mass isotopomer fraction of the isotope on the position x in percent; intensity$_x$=the measured peak intensity or peak area of the metabolic product on the position x; $\sum_{x=m0}^{x=m+n} Intensity_x$=the sum of all peak intensities or peak areas in the predefined mass-range, from the unlabeled mass (M+0) to the complete labeled mass (M+n), which is defined by the maximum number of metabolically accessible atoms of the isotope to be analysed (n); and (e) quantifying the relative amount of labeled metabolic product in the test sample starting from the MIF calculated in step d), wherein:
relative amount of total labeled metabolic product is calculated according to Formula I:

$$L(\%) = \left(1 - \frac{S_L}{R_L}\right) \times 100; \quad (I)$$

and
relative amount of labeled metabolic product labeled at a single position is calculated according to Formulae (II), (II.a) and (II.b)

$$L(\%) = \frac{S_{H\_cor}}{S_{H\_cor} + S_L} \times 100 \quad (II)$$

$$S_{H\_cor} = S_H - S_{L\_Resid} \quad (II.a)$$

$$S_{L\_Resid} = \frac{R_H}{R_L} \times S_L \quad (II.b)$$

wherein L(%)=relative amount of labeled metabolic product in relation to total amount of metabolic product in the test sample; $S_H$=measured relative amount (MIF) of test sample on anticipated heavy position; $S_{H\_corr}$=calculated relative amount (MIF) of heavy mass fragment of test sample corrected for amount of naturally occurring stable isotopes; $S_L$=measured relative amount (MIF) on light position of test sample; $S_{L\_Resid}$=calculated relative amount (MIF) of naturally occurring heavy mass originating from light fragment on anticipated heavy position; $R_H$=measured relative amount (MIF) of reference sample on anticipated heavy position; $R_L$=measured relative amount (MIF) on light position of reference sample.

A "test sample" as used herein denotes a sample which comprises labeled metabolic products that have been generated by labeling methods using labeled substrates.

Manufacturing techniques for the generation of test samples that are suitable for the present application are known in the art. Considered basic steps for manufacturing a test sample suitable for the present application comprise contacting a biological sample with a labeled substrate and removing the labeled substrate prior to quantification of the labeled metabolic products. There is the possibility that, after contacting of the biological sample with the labeled substrate and prior to the quantification step, the labeled metabolic products are extracted, e.g. by one or more purification or isolation steps so that the applied sample is more pure and better suited for further analysis. Preferably, the test samples are manufactured according to a method for preparation of labeled metabolic products of the present invention.

The metabolic products within the test sample may be labeled at a single position or at multiple positions. It must be kept in mind that the metabolic products within the test sample also comprise naturally occurring stable isotopes with a certain probability. "Naturally occurring" in the context of "naturally occurring stable isotopes" means stable isotopes which are present in a natural manner instead of having been incorporated by labeling methods. This shall be explained by the following example: Carbon has two stable isotopes, $^{12}C$ and $^{13}C$, occurring in a natural proportion of approximately 99:1. $^{12}C$ forms approx. 98.9% of all natural carbon on earth while $^{13}C$ forms the remaining approx. 1.1% of all natural carbon on earth. This means that also nominally unlabeled carbon atoms within particular molecules are in fact "naturally" labeled with a probability of 1.1%.

In order to avoid an overestimation in the calculation of stable isotope incorporation into experimentally labeled metabolic products it is necessary to correct for natural occurring stable isotope abundances. This is performed by using reference samples. The term "reference sample" means a sample which comprises only metabolic products with naturally occurring stable isotopes. Manufacturing techniques for the generation of reference samples that are suitable for the present application are known in the art. The reference samples may be manufactured similarly to the test samples with the only difference that the reference samples are not contacted with labeled substrate and therefore do not contain any labeled metabolic products. Considered basic steps for manufacturing a reference sample suitable for the present application comprise contacting a biological sample with an unlabeled substrate and removing the unlabeled substrate prior to quantification of the unlabeled metabolic products. There is the possibility that, after contacting of the biological sample with the unlabeled substrate and prior to the quantification step, the unlabeled metabolic products are extracted, e.g. by one or more purification or isolation steps so that the applied sample is more pure and better suited for further analysis. Preferably, the reference samples are manufactured according to a method for preparation of unlabeled metabolic products of the present invention.

In case the relative amount of labeled metabolic products which are labeled at multiple positions is to be quantified (e.g. metabolic products generated in the tricarboxylic acid cycle), the relative amount of total label can be calculated from the amount of disappearing intensity of the light fragment in the test sample ($S_L$) compared to light fragment in the reference sample ($R_L$) (Formula I) which contains the summed up information of the incorporated label at all positions. The amount of total label can be calculated from the amount of disappearing intensity of the light mass fragment of the sample ($S_L$) compared to the light mass fragment in the reference sample ($R_L$).

A "light mass fragment" as used herein means a molecule fraction which has incorporated no isotope with increased molecular weight and corresponds to the M+0 peak in the mass spectrum analysis.

A "heavy mass fragment" as used herein means a molecule fraction which has incorporated one or more isotopes with increased molecular weight, e.g. $^{13}C$, and is represented by a mass-shift relative to the M+0 peak in the mass spectrum analysis. For example, if one isotope with increased molecular weight is incorporated this corresponds to the M+1 peak in the mass spectrum analysis, if two isotopes with increased molecular weight are incorporated this corresponds to the M+2 peak in the mass spectrum analysis etc.

Quantification of the relative amount of labeled metabolic products which are labeled at a single position is more complicated: Starting from MIF, the label incorporation is defined as the ratio of the intensity of the monitored heavy labeled mass fragment of the sample ($S_H$) to the sum of the intensities of the heavy and light mass fragment of the sample ($S_L$). Unfortunately, this simple calculation could lead to an overestimation of label incorporation due to naturally occurring carbon, nitrogen and silicone isotopes in the derivatised metabolic products of the test sample. The consideration of mass spectra from reference samples provides the correction term for natural isotope abundance (Formula II.a) by multiplying the ratio of heavy mass fragment of reference sample ($R_H$) to the light mass fragment of reference sample ($R_L$) with the intensity of the light mass fragment in the sample ($S_L$) (Formula II.b). The relative amount of heavy mass fragment of test sample corrected for amount of naturally occurring stable isotope abundances is then used to calculate the labeling (Formula II). This calculation assumes the compounds to be labeled at a single position (which holds true for e.g. glycolytic metabolic products after application of $^{13}C_1$-glucose).

The present invention is also directed to a method for quantification of a labeled metabolic product from a biological sample, comprising the steps: (a) providing a test sample comprising a labeled metabolic product produced according to a method for preparation of labeled metabolic products of the present invention; (b) providing a reference sample comprising unlabeled metabolic product, preferably produced according to a method for preparation of unlabeled metabolic products of the present invention, wherein the labeled substrate is omitted or replaced by unlabeled substrate; (c) determining mass spectra of the test sample of step a) and of the reference sample of step b); (d) calculating corresponding mass isotopomer fractions (MIF) for test and reference sample based on respective peak intensities or peak areas extracted from mass spectra of step c) preferably according to Formula (0);

$$MIF_x = \frac{\text{Intensity}_x}{\sum_{x=m0}^{x=m+n} \text{Intensity}_x} * 100\% \quad (0)$$

wherein $MIF_x$=mass isotopomer fraction of the isotope on the position x in percent; intensity$_x$=the measured peak intensity or peak area of the metabolic product on the position x; $\Sigma_{x=m0}^{x=m+n}$Intensity$_x$=the sum of all peak intensities or peak areas in the predefined mass-range, from the unlabeled mass (M+0) to the complete labeled mass (M+n), which is defined by the maximum number of metabolically accessible atoms of the isotope to be analysed (n); and (e) quantifying the relative amount of labeled metabolic product in the test sample starting from the MIF calculated in step d), wherein:
relative amount of total labeled metabolic product is calculated according to Formula I:

$$L(\%) = \left(1 - \frac{S_L}{R_L}\right) \times 100; \quad (I)$$

and
relative amount of labeled metabolic product labeled at a single position is calculated according to Formulae (II), (II.a) and (II.b)

$$L(\%) = \frac{S_{H\_cor}}{S_{H\_cor} + S_L} \times 100 \quad (II)$$

$$S_{H\_cor} = S_H - S_{L\_Resid} \quad (II.a)$$

$$S_{L\_Resid} = \frac{R_H}{R_L} \times S_L \quad (II.b)$$

wherein L(%)=relative amount of labeled metabolic product in relation to total amount of metabolic product in the test sample; $S_H$=measured relative amount (MIF) of test sample on anticipated heavy position; $S_{H\_corr}$=calculated relative amount (MIF) of heavy mass fragment of test sample corrected for amount of naturally occurring stable isotopes; $S_L$=measured relative amount (MIF) on light position of test sample; $S_{L\_Resid}$=calculated relative amount (MIF) of naturally occurring heavy mass originating from light fragment on anticipated heavy position; $R_H$=measured relative amount (MIF) of reference sample on anticipated heavy position; $R_L$=measured relative amount (MIF) on light position of reference sample.

The present invention is also directed to a method for quantification of a labeled metabolic product from a biological sample, comprising the steps of: (a) determining mass spectra of a test sample and of a reference sample; (b) calculating corresponding mass isotopomer fractions (MIF) for the test and the reference sample based on respective peak intensities or peak areas extracted from mass spectra of step a) preferably according to Formula (0);

$$MIF_x = \frac{\text{Intensity}_x}{\sum_{x=m0}^{x=m+n} \text{Intensity}_x} * 100\% \quad (0)$$

wherein $MIF_x$=mass isotopomer fraction of the isotope on the position x in percent; intensity$_x$=the measured peak intensity or peak area of the metabolic product on the position x; $\Sigma_{x=m0}^{x=m+n}$Intensity$_x$=the sum of all peak intensities or peak areas in the predefined mass-range, from the unlabeled mass (M+0) to the complete labeled mass (M+n), which is defined by the maximum number of metabolically accessible atoms of the isotope to be analysed (n); and (c) quantifying the relative amount of labeled metabolic product in the test sample starting from the MIF calculated in step b), wherein:
relative amount of total labeled metabolic product is calculated according to Formula I:

$$L(\%) = \left(1 - \frac{S_L}{R_L}\right) \times 100; \quad (I)$$

and
relative amount of labeled metabolic product labeled at a single position is calculated according to Formulae (II), (II.a) and (II.b)

$$L(\%) = \frac{S_{H\_cor}}{S_{H\_cor} + S_L} \times 100 \quad (II)$$

-continued $$S_{H\_cor} = S_H - S_{L\_Resid} \quad \text{(II.a)}$$

$$S_{L\_Resid} = \frac{R_H}{R_L} \times S_L \quad \text{(II.b)}$$

wherein L(%)=relative amount of labeled metabolic product in relation to total amount of metabolic product in the test sample; $S_H$=measured relative amount (MIF) of test sample on anticipated heavy position; $S_{H\_corr}$=calculated relative amount (MIF) of heavy mass fragment of test sample corrected for amount of naturally occurring stable isotopes; $S_L$=measured relative amount (MIF) on light position of test sample; $S_{L\_Resid}$=calculated relative amount (MIF) of naturally occurring heavy mass originating from light fragment on anticipated heavy position; $R_H$=measured relative amount (MIF) of reference sample on anticipated heavy position; $R_L$=measured relative amount (MIF) on light position of reference sample.

The present invention is also directed to a method for quantification of a labeled metabolic product from a biological sample, comprising the steps of: (a) calculating mass isotopomer fractions (MIF) for a test sample and for a reference sample based on respective peak intensities or peak areas extracted from mass spectra of the test sample and of the reference sample preferably according to Formula (0);

$$MIF_x = \frac{\text{Intensity}_x}{\sum_{x=m0}^{x=m+n} \text{Intensity}_x} * 100\% \quad \text{(0)}$$

wherein $MIF_x$=mass isotopomer fraction of the isotope on the position x in percent; intensity$_x$=the measured peak intensity or peak area of the metabolic product on the position x; $\sum_{x=m0}^{x=m+n}$Intensity$_x$=the sum of all peak intensities or peak areas in the predefined mass-range, from the unlabeled mass (M+0) to the complete labeled mass (M+n), which is defined by the maximum number of metabolically accessible atoms of the isotope to be analysed (n); and (b) quantifying the relative amount of labeled metabolic product in the test sample starting from the MIF calculated in step a), wherein:

relative amount of total labeled metabolic product is calculated according to Formula I:

$$L(\%) = \left(1 - \frac{S_L}{R_L}\right) \times 100; \quad \text{(I)}$$

and relative amount of labeled metabolic product labeled at a single position is calculated according to Formulae (II), (II.a) and (II.b)

$$L(\%) = \frac{S_{H\_cor}}{S_{H\_cor} + S_L} \times 100 \quad \text{(II)}$$

$$S_{H\_cor} = S_H - S_{L\_Resid} \quad \text{(II.a)}$$

$$S_{L\_Resid} = \frac{R_H}{R_L} \times S_L \quad \text{(II.b)}$$

wherein L(%)=relative amount of labeled metabolic product in relation to total amount of metabolic product in the test sample; $S_H$=measured relative amount (MIF) of test sample on anticipated heavy position; $S_{H\_corr}$=calculated relative amount (MIF) of heavy mass fragment of test sample corrected for amount of naturally occurring stable isotopes; $S_L$=measured relative amount (MIF) on light position of test sample; $S_{L\_Resid}$=calculated relative amount (MIF) of naturally occurring heavy mass originating from light fragment on anticipated heavy position; $R_H$=measured relative amount (MIF) of reference sample on anticipated heavy position; $R_L$=measured relative amount (MIF) on light position of reference sample.

The present invention is also directed to the use of the methods for preparation of labeled metabolic products and for quantification of labeled metabolic products of the present invention for analysing metabolic products in biological samples. These methods have several advantages over the state of the art: First, the provided sample preparation method preserves the metabolic homeostasis during cell harvest due to continuous supply of major nutrients. Second, the short incubation times for labeling of metabolic products allow measurements of the metabolic activity and its changes in short time scales, e.g. minutes. This provides the opportunity to detect transient metabolites or to test the direct impact of different substances, e.g. medicaments, drugs, small molecules, metabolic inhibitors etc. on the metabolic network rather than characterizing compensatory reactions of the cell system after long incubation periods. Furthermore, direct determination of differences between altered cell conditions or between cell lines can be performed which might bring new information about potential cellular targets for diagnostic and therapeutic approaches. Third, the provided calculation method makes it possible to determine stable isotope incorporation into experimentally labeled metabolic products by correcting for natural occurring stable isotope abundances. This approach does not require prior knowledge of the chemical composition of the sample and facilitates the analysis of stable isotope incorporation into unknown compounds.

The present invention is also directed to the use of the methods of the present invention for preparation of labeled metabolic products and for quantification of labeled metabolic products for analysing the effect of small molecules on metabolic processes. According to the present invention, the small molecules may be added to the biological sample at different time points e.g. prior, during or after labeling of the biological sample and/or combinations thereof. Small molecules are crucial research tools to study biological functions as well as for development of new chemical, nutritional, therapeutic or diagnostic agents. The application of the methods of the present invention in combination with small molecules may resolve the molecular targets of small molecules within the metabolic network and helps to define their exact mode of action.

FIGURES

FIGS. 1a, 1b, 1c, 1d, and 1e—Sample preparation, identification and quantification of metabolic products. (FIG. 1a) Scheme of the experimental workflow from cell culture, harvest to GC-MS measurement. (FIG. 1b) A representative GC-MS selected ion chromatogram obtained from a cell culture sample using temperature-controlled injection. Due to the method peaks of pyruvic and lactic acid can be baseline separated detected and quantified. The majority of phosphates are distinguishable over a broad mass range, even with high structural similarity. (FIG. 1c) Distribution of the coefficient of variation (CoV) of the measured metabolite quantities from five measured biological replicates, distinct compound classes are indicated. (FIG. 1d) Spike in experiment in order to test the technical recovery of metabolites. Therefore samples were measured alone and with spiked in quantification mixtures at eight concentrations. (FIG. 1e) Metabolite profile of T98G cells ranked with elevated quantities. Some central intermediates are indicated.

FIGS. 2a, 2b, 2c, and 2d,—Workflow and results of heavy isotope incorporation. (FIG. 2a) Data analysis workflow from GC-MS raw data up to quantification and the calculation of $^{13}C$-label incorporation. (FIG. 2b) Map of the central carbon metabolism highlighting detection, quantification of intermediates as well as evaluation of stable isotope enrichment after application of $^{13}C$-glucose or $^{13}C$-glutamine in cell culture experiments. (FIG. 2c) Nomenclature and mathematical definitions are shown for the determination of isotope incorporation based on the MIF in a reference sample (left panel) and labeled test sample (right panel, $^{13}C_1$-glucose, ratio $^{12}C$:$^{13}C$ 50%). The label incorporation (L in (%) can be determined position independent (Formula I) and position-dependent (Formulae II, II.a, II.b). (FIG. 2d) Formulae were validated by the measurement and analysis of known ratios of $^{12}C$ glucose:$^{13}C_1$-glucose. Shown are expected versus measured stable isotope incorporation comparing both strategies and correction for natural isotope abundance.

Figure 3:
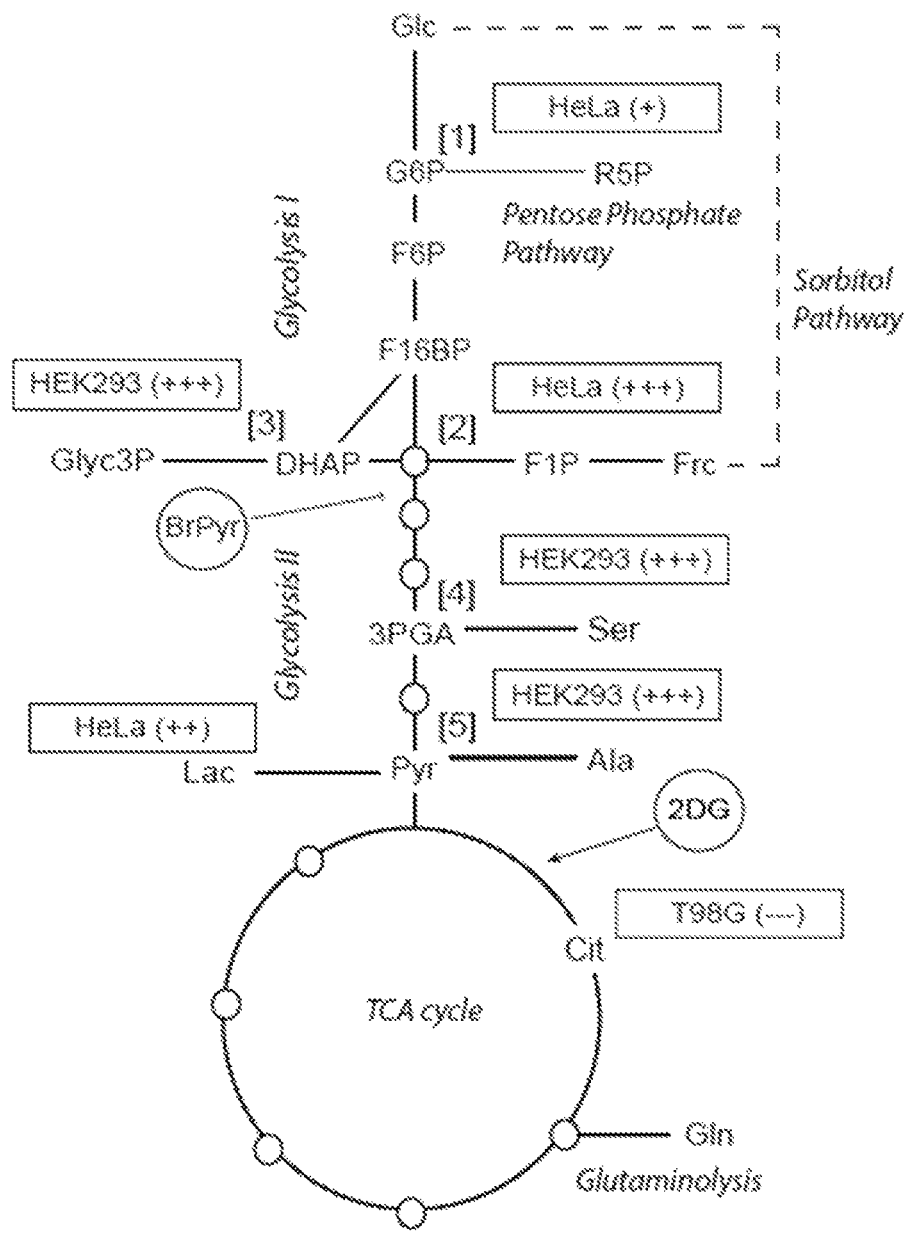
Figure 3:
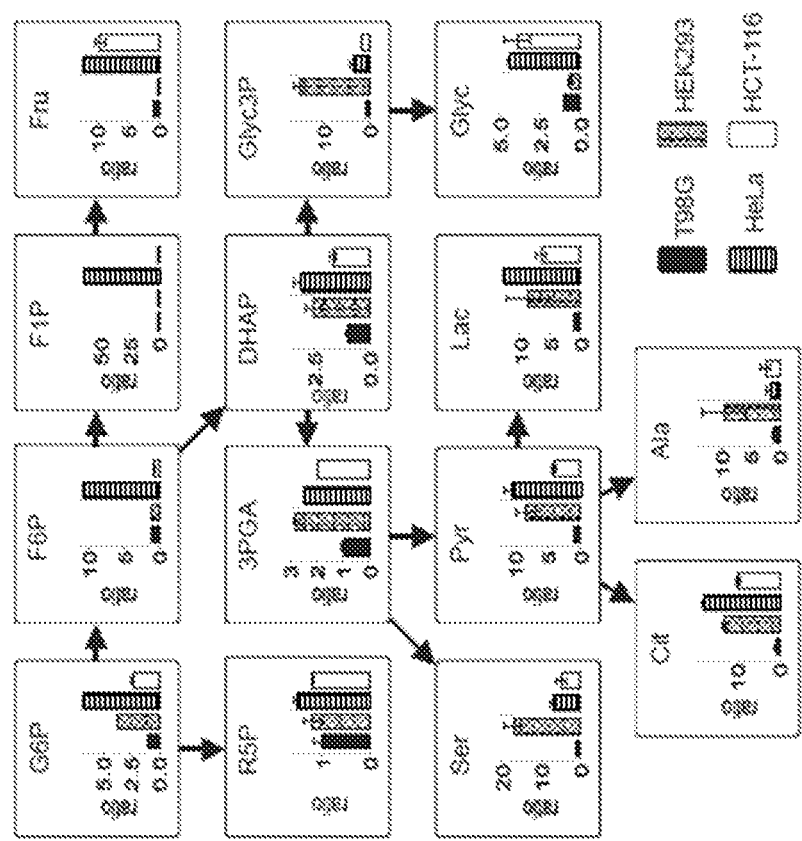
Figure 3:
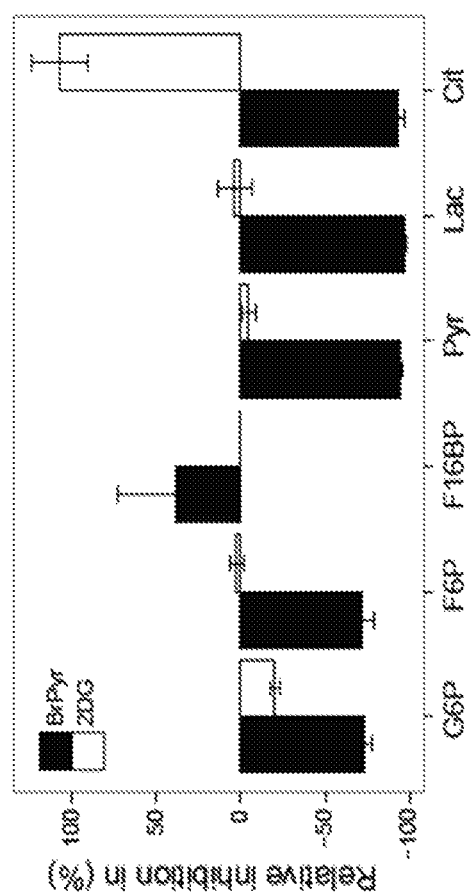

FIGS. 3a, 3b, and 3c—Application of pSIRM for the comparison of carbon routing in cell lines or monitoring influence of inhibitory treatment. (a) Summarizing the results of carbon routing at branching points [1-5] in different cell lines, and potential impact of BrPyr or 2DG (T98G only) in central carbon metabolism. (b) Quantification of $^{13}C_6$-glucose incorporation within metabolic intermediates (labeled quantity per $1 \times 10^5$ cells/min) of T98G, HEK293, HeLa cells and HCT-116 cells. Arrows between metabolites indicate the link within network. The data are presented relative to T98G cells. (c) Visualization of the pSIRM analysis ($^{13}C$-Glucose, 3 min) of the inhibitory activity of BrPyr and 2DG (both 2 mM, 15 min) on T98G cells. $^{13}C$-incorporation was compared to control (PBS-treatment) samples.

EXAMPLES

Materials and Methods
Chemicals

Stable isotope labeled substrates u-$^{13}C$-Glucose and $^{13}C_1$-Glucose were purchased at Campro Scientific (Germany). Extraction chemicals methanol and chloroform were products of Merck. All other chemicals were bought in highest quality at Sigma-Aldrich unless otherwise noted.
Cell Culture T98G, HeLa, HCT-116 and HEK293 cell lines were cultivated in glucose-free DMEM (Invitrogen) supplemented with 2.5 g/L glucose, 10% fetal bovine serum (Invitrogen), 1% Penicillin/Streptomycin (Invitrogen) and cultivated at 37° C., 5% $CO_2$. Cells were passaged with appropriate split ratios every three days. Viable cell numbers were determined by trypan blue staining (0.04%, Invitrogen) and automated counting (BioRad).
GC-MS Analysis Retention index standards: Nine alkanes (n-decane, n-dodecane, n-pentadecane, n-octadecane, n-nonadecane, n-docosane, n-octacosane, n-dotriacontane, n-hexatriacontane) were dissolved in hexane, combined at a final concentration of 2 mg/ml and stored at 4° C. Retention index standard was added to the solvent (MSTFA) at a final concentration 2% v/v during derivatization.

Quantification standard: The quantification mixture was composed of 45 compounds (stock concentration 1 mg/ml, 50% MeOH). A dilution series from 1:1, 1:2, 1:5, 1:10, 1:20, 1:50, 1:100 and 1:200 were prepared, aliquoted, dried under vacuum and stored at −20° C. One set of quantification standard was treated parallel to cell extracts during derivatization and measured in technical replicates within an experiment.

Derivatization: Dried cell extracts were resolved in 20 μl of methoxyamine hydrochloride-solution (Sigma, 40 mg/ml in pyridine (Roth)) and incubated for 90 min at 30° C. constantly shaking followed by the addition of 80 ul of N-methyl-N-[trimethylsilyl]trifluoroacetamide (MSTFA, Machery-Nagel) and incubation at 37° C. for 45 min. Extracts were centrifuged for 10 min at 10.000×g and aliquots of 30 ul were transferred into glass vials (Th. Geyer) for GC-MS measurement.

GC-MS measurement: Metabolite analysis was performed on a gas chromatography coupled to time of flight mass spectrometer (LECO-Pegasus III— TOF-MS-System, LECO), supplemented with an auto-sampler (MultiPurpose Sampler 2 XL, Gerstel). Samples and quantification standards were injected in split mode (split 1:5, injection volume: 1 ul,) in a temperature-controlled injector (CAS4, Gerstel) with a baffled glass-liner (Gerstel). The following temperature program was applied during sample injection: Initial temperature of 80° C. for 30 s followed by a ramp with 12° C./min to 120° C. and a second ramp with 7° C./min to 300° C. and final hold for 2 min. Gas chromatographic separation was performed on an Agilent 6890N (Agilent), equipped with a Varian VF-5 ms-column of 30 m length, 250 μm inner diameter and 0.25 μm film thickness (Varian). Helium was used as carrier gas with a flow rate of 1.2 mL/min. Gas chromatography was performed with the following temperature gradient: 2 min heating at 70° C., first temperature gradient with 5° C./min up to 120° C. and hold for 30 s, subsequently a second temperature increase of 7° C./min up to 350° C. with a hold time of 2 min. Spectra were recorded in a mass range of 60 to 600 u with 20 spectra/s at a detector voltage of 1750 V.

Data analysis: The vendor software ChromaTOF Version 4.42 (LECO Corp. St. Joseph—USA) was used for metabolite evaluation with the following parameter: baseline offset of 1, peak width of 4 s, signal/noise of 20, peak smoothing of 11 data-points. Retention indices were calculated based on retention index standards as described (Ref). Golm Metabolome Database (GMD) provided peak identification. The quantification routine of ChromaTOF was used for external calibration based on the measured quantification standards. Exported csv-files included: Name, quant mass, retention index, 1st dimension retention time, 2nd dimension retention time, area, concentration, match, reverse, quant signal/noise, type, concentration units and the peak true spectrum in absolute values. For further data analysis the tool MetMax was developed in cooperation with the MPIMP in Potsdam-Golm (http://gmd.mpimp-golm.mpg.de/apps/metmax). MetMax provided of extraction of peak areas and quantities (retention analysis mode), and intensities of pre-defined mass ranges (isotope concentrator mode) from the exported csv-files. The in-house developed pSIRM-wizard enabled the determination of $^{13}C$-label incorporation based on the exported data following the descriptions and equations stated in the paper.

Experimental Procedures

Cell harvest: Growth media was removed from cells and cells were incubated in 5 ml of prewarmed (37° C.) wash-buffer (137 mM NaCl, 3 mM KCl, 5 mM HEPES, adjusted to a pH of 7.2-7.4) enriched with the same amount of glucose and glutamine as in the growth media (2.5 g/L and 4 mM respectively). For the metabolic labeling the wash-buffer is used as labeling buffer with glucose or glutamine replaced by their $^{13}$C-counterpart. Cells were incubated for 3 minutes at 37° C. before harvest. The buffer was removed followed by an immediate addition of 5 ml of prechilled (−20 to −40° C.) 50% MeOH (with 2-4 μg/mL Cinnamic acid as internal standard) to the plate. Cells were scratched of the plates using cell-scraper and transferred to a falcon, which contain 1 ml of chloroform. Cell suspension was frozen in liquid nitrogen and stored at −80° C. until extraction. To extract cell metabolism the suspension was shaken for 30 minutes at 4° C., followed by a centrifugation for 10 minutes to perform phase separation. 4.5 ml of the upper, polar phase were transferred into a new falcon and dried under vacuum. On the next day the pellet was resuspended in 530 μl 20% Methanol (4° C.), shaken at 4° C. until completely solved, transferred into two eppies (2×250 μl) and dried under vacuum. The dried samples were stored at −20° C. and derivatized as described above.

Reproducibility: T98G cells were seeded (6.5×10$^5$ cells per 10 cm cell culture dish) in 10 ml DMEM (2.5 g/L glucose, 4 mM glutamine, 10% FBS, 1% Pen/Strep) and cultivated for three days. Media changes were performed 24 and 4 hours prior the harvest to avoid nutrient deprivation. Stable isotope labeling with $^{13}$C-Glucose was applied at three independent dishes for 3 min. Cell harvest and extraction was carried out as described above. Cell numbers were determined with two additional dishes. Derivatization extracts of all dishes were pooled, aliquoted and measured six-times to evaluate technical reproducibility. The biological variance was determined by the cultivation and treatment of T98G cells as before on five 10 cm dishes and GC-MS measurement in four technical replicates. In addition two plates of T98G cells were harvested equally with $^{12}$C-Glucose for the acquisition of unlabeled reference spectra.

Quant-Addition: Seven dishes of T98G cells were harvested as described above. Cell extracts were extracted a second time with 20% v/v MeOH containing an internal standard (cinnamic acid, 2 μg/ml), and pooled. Five aliquots of 280 uL were dried under vacuum. Other 280 uL of this pool were added two one dilution of quantification mix each and dried afterwards under vacuum. Two complete sets of the quantification mix were treated in the same way like the biological extracts and dried. Latter ones were used to determine calibration curves for the quantification of all samples.

Experimental verification of correcting strategies by mixing $^{13}$C$_1$ with $^{12}$C-glucose: Individual stock solutions of $^{12}$C-glucose and an equimolar amount of $^{13}$C$_1$-glucose were prepared and were tested by drying the same volumes. The $^{12}$C and $^{13}$C solutions were mixed in different ratios in triplicates, dried, derivatized, measured on the GC-MS and analysed as described above.

Metabolic profiling of cell lines: T98G, HEK293, HeLa and HCT-116 were grown for the analysis of the metabolic profile under identical nutrient conditions (DMEM, 10% FBS, 2.5 g/L glucose, 4 mM glutamine). Seeding densities were evaluated in advance to avoid contact inhibition. Three dishes per each cell lines were pooled, processed as described above and measured in technical replicates.

Glycolytic inhibition: T98G cells were seeded as described before and cultivated for 24 hrs. Inhibitors were added in the following concentrations separately for 12 min: 2 mM BrPyr and 2, 4 and 10 mM 2 DG. On a separate dish 2 mM mannitol were applied as osmotic control. Subsequently, media was replaced with 5 ml pre-warmed labeling buffer containing 2.5 g/L u-$^{13}$C-glucose, 2 mM glutamine and inhibitors in the same concentration range as added before for other 3 min. Cell harvest, extraction and metabolite measurement were performed as described.

Results

Central Carbon Metabolism (CCM) comprises a large number of small molecules differing in their chemical properties, making detection and quantification of all intermediates using a single technique challenging. We have further developed GC-MS based metabolomics to measure the intermediates of CCM with high coverage, in absolute quantities, and to extract isotope information from the fragment spectra. This improved workflow (FIGS. 1a and 2a) builds the basis for pulsed stable isotope resolved metabolomics (pSIRM). We further refined the chromatography in order to detect and quantify CCM intermediates. We specifically identified conditions for the reliable separation and quantification of pyruvate and lactate (FIG. 1b). Further improvements were made using a thermo-regulated injector, resulting in the temperature-dependent transfer of compounds from the liner to the column, and by optimizing temperature program and gas-flow (see methods and supplemental material).

Example 1

Cell Harvest Strategy

The separation of mammalian cell cultures from nutrient rich culture medium without disturbing the cellular metabolic homeostasis is crucial. We designed a cell harvesting strategy aimed at preserving the metabolic homeostasis during harvest: (i) exchange of culture medium prior to pSIRM experiment (2-4 hours) to minimize concentration changes of nutrients during stable isotope pulse labeling and (ii) the continuous supply of major nutrients during the whole harvest, preventing the disruption of glycolysis or glutaminolysis. Depending on the time of label incorporation stable isotope labeled substrates are either added to a full label medium containing all factors and nutrients or to a labeling buffer containing main nutrients, buffers and salts to maintain osmolality and pH. In both cases one major nutrient is replaced by a carbon-13 variant. The usage of labeling buffer for pSIRM experiments is appropriate for incubation times up to 5 minutes, but for longer experiments a full label medium is suggested. Adherent cell lines can be labeled growing attached to their plates. Growth medium is replaced with pre-warmed full label medium. After incubation cells are rinsed with wash-buffer for a few seconds. Immediately pre-cold methanol (50% v/v, −20° C.) quenches all cellular processes directly and initiates metabolite extraction (see methods).

Figure 1C:
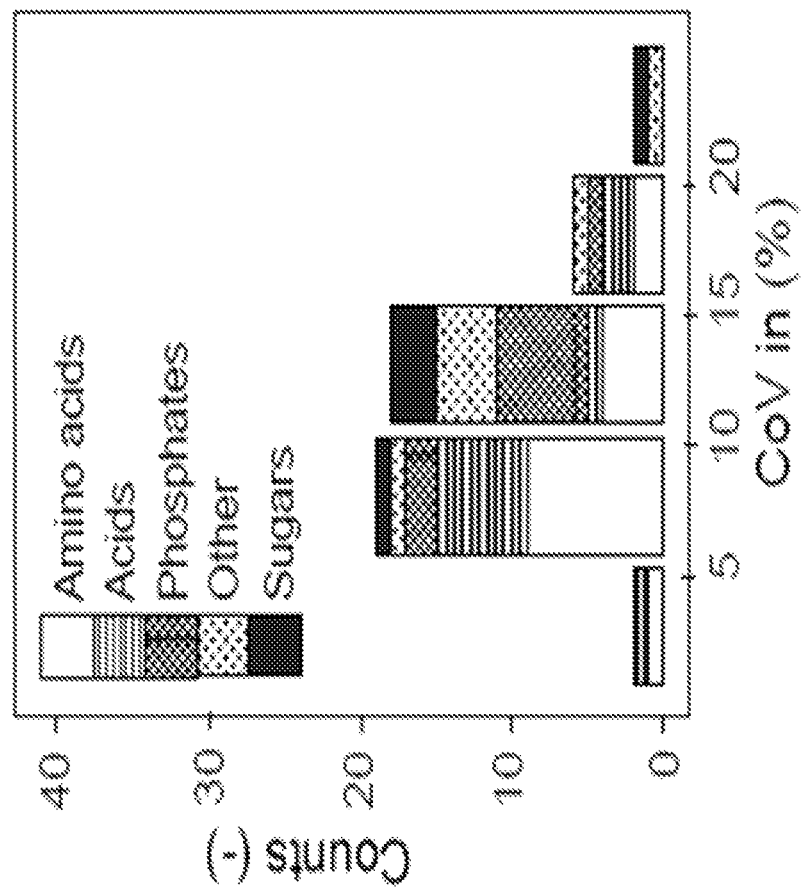

In order to test the reproducibility of metabolite quantification, T98G cells were harvested as described, pooled and measured six times independently, giving the technical variance of the method. Five independently grown plates were treated separately during harvest and labeling, as well as metabolite extraction and measured in three technical replicates to evaluate the biological reproducibility. We observed that 80% of metabolites displayed a variation below 15% (FIG. 1c).

Example 2

Quantification of CCM Metabolites

Figure 1D:
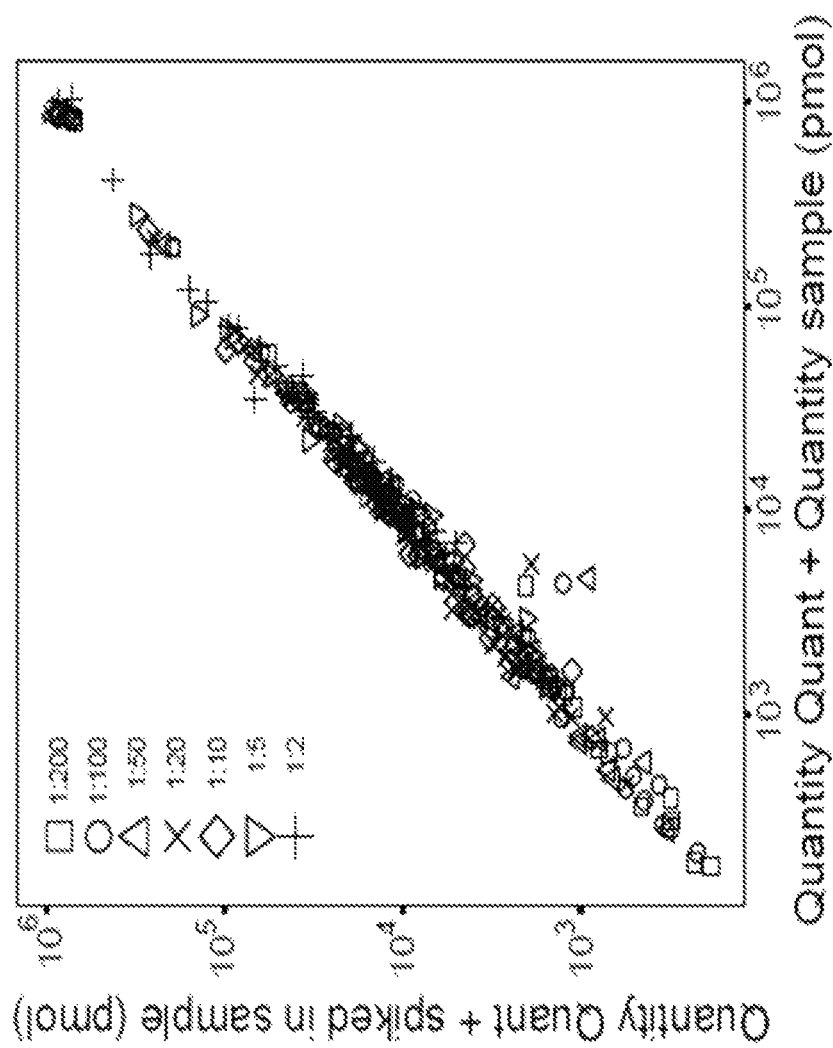
Figure 1E:
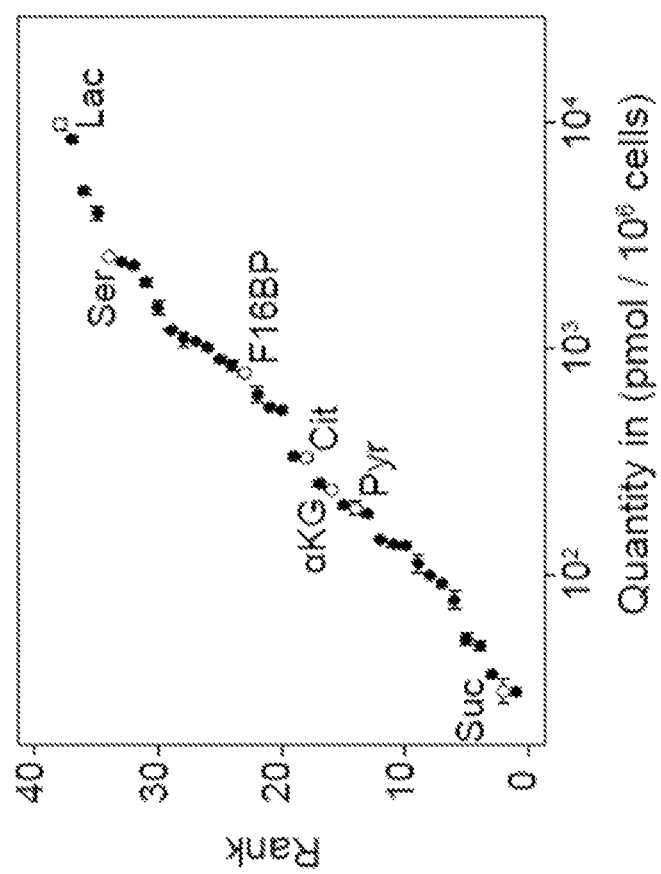

Absolute quantification of metabolites improves metabolomics analyses; it may enable inter-batch and inter-laboratory comparison and is a prerequisite for quantitative modeling. Different methods for absolute quantification have been described: isotopic dilution is often applied for LC-MS based quantification. This strategy enables correcting for strong matrix effects and ion suppression. However, the experimentally introduced isotopically-labeled substances may interfere with the measurement of isotopomer distributions for metabolic flux analyses making it necessary to run different measurements for quantification and isotopomer extraction. Electron impact ionization (EI) is the standard ionization technique used for gas chromatography coupled mass spectrometry (GC-MS). This harsh ionization allows monitoring even of uncharged molecules, such as alkanes, and suffers less from ion suppression. In order to quantify metabolites, we established calibration curves using known quantities of a mixture of metabolites, mimicking the composition of the cellular metabolome. This mixture was measured in eight different dilutions, resulting in 45 calibration curves with $R^2>0.95$. Recovery and quantification of metabolites can be influenced by several factors. To test the accuracy and concentration range suitable for quantification we performed a "spike-in" experiment using the quantification mixture and cell extracts. We thus measured the quant-mixture and biological extracts separately as well as the biological extract with spiked-in quant-mixture. The comparison of the derived concentration values demonstrates the reliability of our approach in regard to matrix interactions and concentration ranges for the selected compounds (FIG. 1d).

Example 3

Determination of Time Resolved Isotope Incorporation Rates

Figure 2:
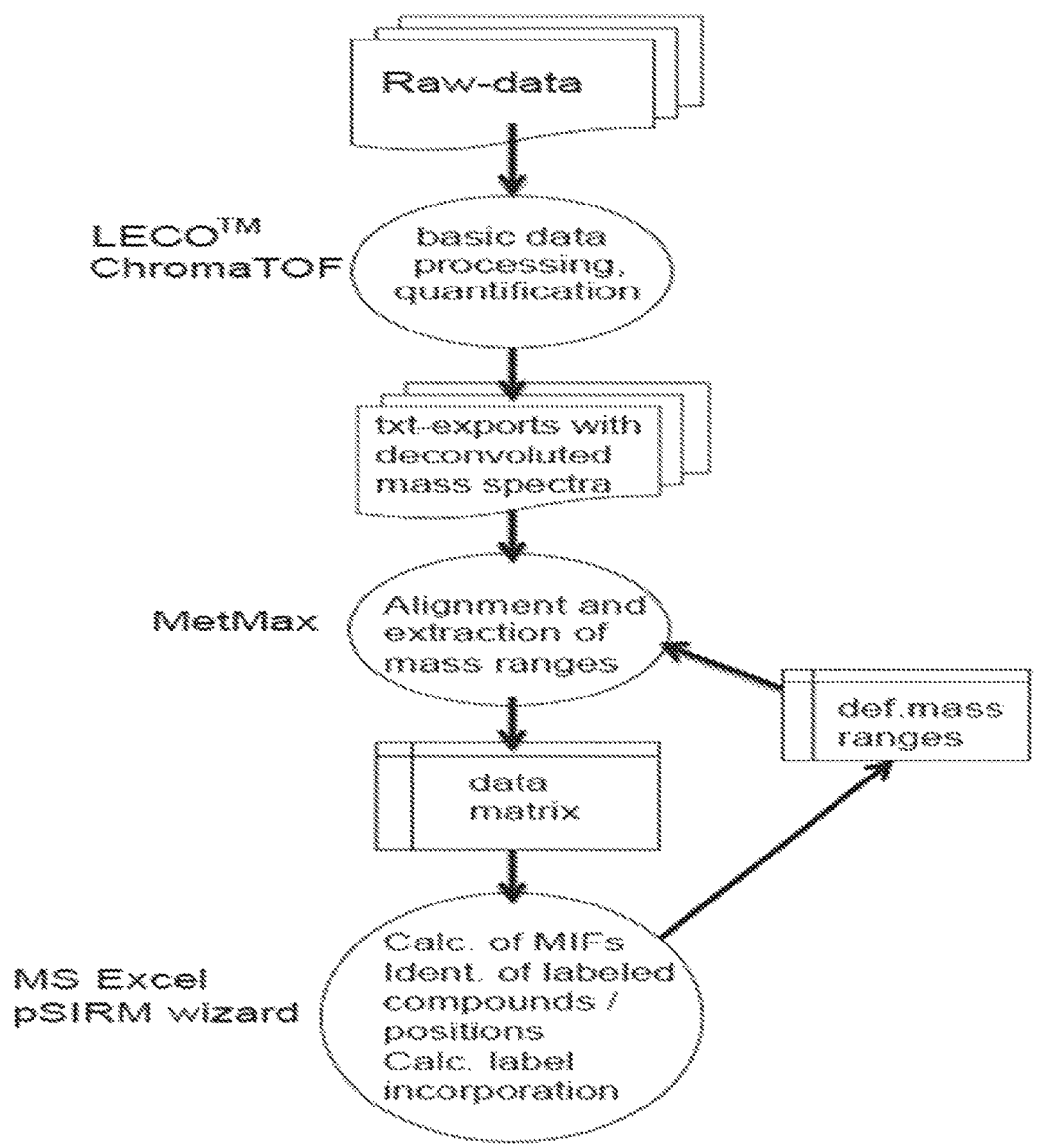
Figure 2:
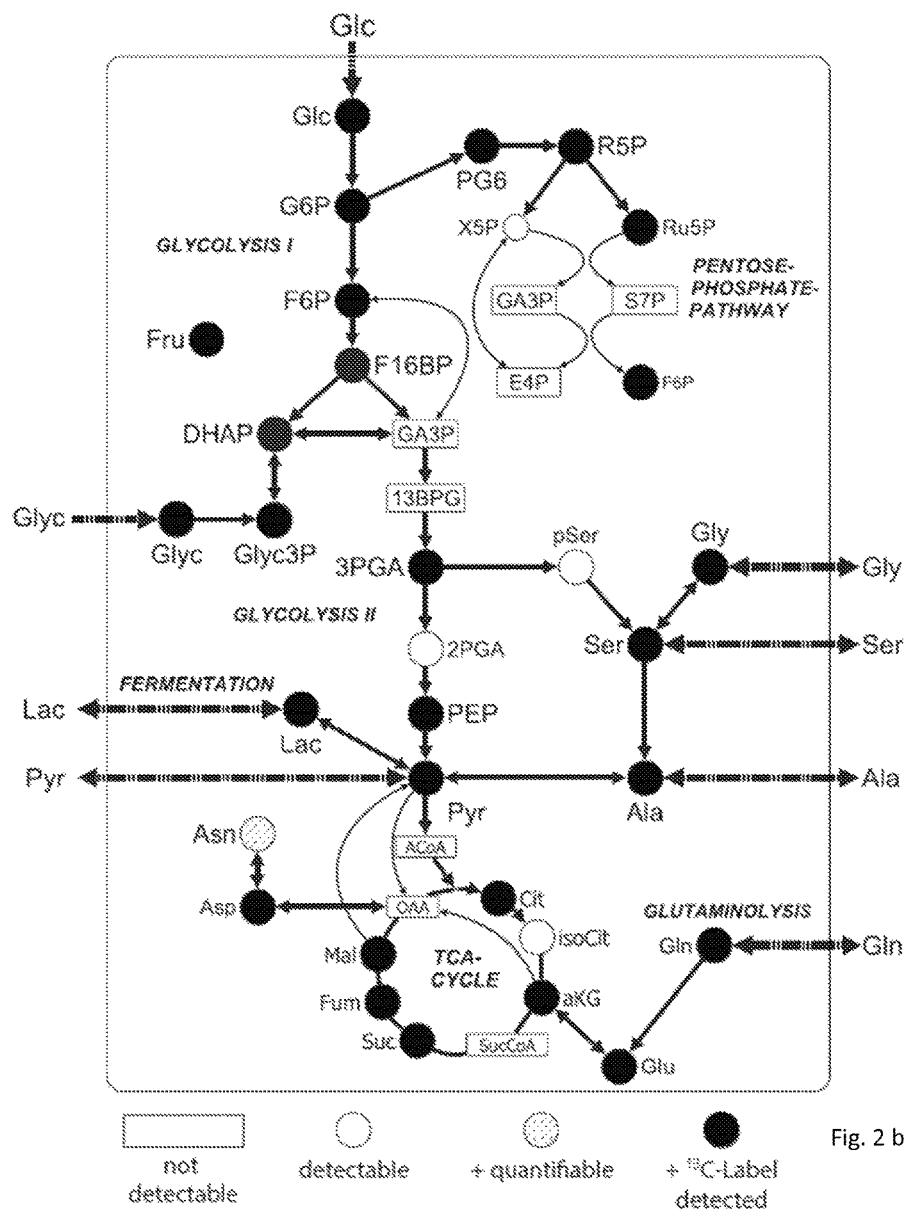
Figure 2:
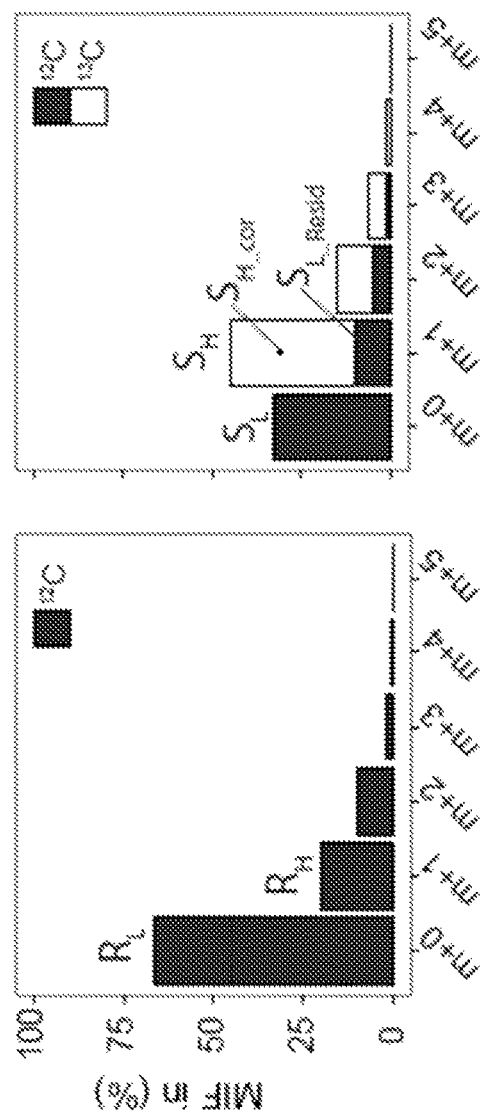
Figure 2:
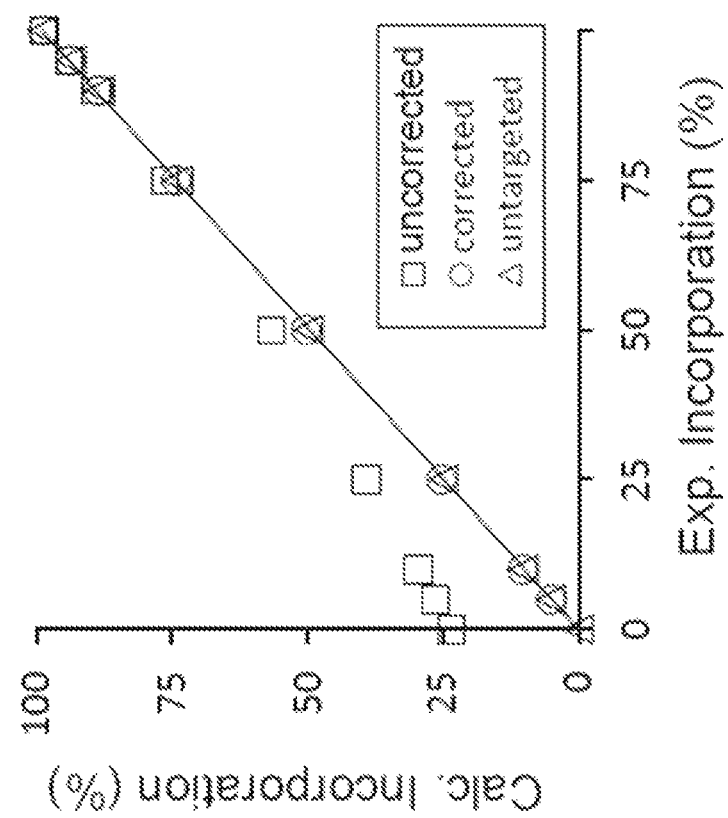

The concept of mass isotopomer analysis relies on the information about the incorporation of heavy carbon atoms in the metabolite pools, which is inherited within the intensity shift between isotopomers in the mass spectra. A prerequisite for a reliable analysis of isotopomers is the extraction of the corresponding mass spectra from GC-MS chromatograms. To determine the stable isotope incorporation in intermediates of CCM we have established the pSIRM data analysis workflow. With this approach the quantity of a compound and the degree of stable isotope incorporation can be determined from the peak intensities and distribution of the mass isotopomers within the same measurement (FIG. 2B). We generated a list of mass pairs for the calculation of stable isotope incorporation based on our experimental results (Table 1).

TABLE 1

Identified pairs of mass fragments used for the determination of $^{13}$C-stable isotope incorporation.

| | | | Mass fragment (m/z) | | |
|---|---|---|---|---|---|
| Compound | Derivate | Abbr. | Unlabeled | Labeling with u-$^{13}$C-glucose | Labeling with u-$^{13}$C-glutamine |
| Alanine | 3TMS | Ala | 188 | 190 | — |
| Aspartic acid | 3TMS | Asp | 232 | 235 (a) | — |
| Citric acid | 4TMS | Cit | 273 | 275 | 277 |
| Dihydroxyacetone phosphate | 1MeOX 3TMS | DHAP | 400 | 403 | — |
| Fructose | 1MeOX 5TMS | Fru | 217 | 220 | — |
| Fructose-1,6-bisphosphate | 1MeOX 7TMS | F16BP | 217 | 220 | — |
| Fructose-6-phosphate | 1MeOX 6TMS | F6P | 217 | 220 | — |
| Fumaric acid | 2TMS | Fum | 245 | 247 | 249 |
| Glucose | 1MeOX 5TMS | Glc | 319 | 323 | — |
| Glucose-6-phosphate | 1MeOX 6TMS | G6P | 217 | 220 | — |
| Gluconic acid-6-phosphate | 7TMS | PG6 | 217 | 220 | — |
| Glutamic acid | 3TMS | Glu | 246 | — | 250 |
| Glutamine | 3TMS | Gln | 156 | — | 160 |
| Glutaric acid | 2TMS | Glut | 261 | — | 266 |
| Glutaric acid, 2-hydroxy | 3TMS | Glut-OH | 247 | — | 251 |
| Glutaric acid, 2-oxo | 1MeOX 2TMS | aKG | 198 | 200 | 203 |
| Glyceric acid-3-phosphate | 4TMS | 3PGA | 357 | 359 | — |
| Glycerol | 3TMS | Glyc | 218 | 221 | — |
| Glycerol-3-phosphate | 4TMS | Glyc3P | 357 | 359 | — |
| Glycine | 3TMS | Gly | 276 | 277 | — |
| Lactic acid | 2TMS | Lac | 117 | 119 | — |
| Malic acid | 3TMS | Mal | 233 | 235 | 236 |
| Phosphoenolpyruvic acid | 3TMS | PEP | 369 | 372 | — |
| Pyruvic acid | 1MeOX 1TMS | Pyr | 174 | 177 | — |
| Ribose-5-P | 1MeOX 5TMS | R5P | 217 | 220 | — |
| Serine | 3TMS | Ser | 204 | 206 | — |
| Succinic acid | 2TMS | Suc | 247 | 249 | 251 |

(a) when simultaneously applied with 13C-glutamine labeling, the resulting 13C-pyroglutamate might interfere with this mass range.

To analyse the quantitative isotopomer distribution of the corresponding fragments, peak lists including the mass-spectral information were generated with the vendor software ChromaTOF, and exported as tab-separated txt-files. These files were imported into MetMax-Software for mass isotopomer distributions extraction. Mass isotopomer fractions (MIF) were calculated based on the extracted intensities within substance-specific defined mass ranges (see Table 2).

TABLE 2

Exemplary calculation of isotope incorporation using the targeted strategy.
$^{13}C_1$-Glucose and $^{12}C$-glucose were mixed in known ratios to proof the targeted calculation strategy. Two examples of calculations are shown for the determination of $^{13}C$-abundance as described.

| | Intensities in (ion counts) | | | MIF in (%) | | | 10% $^{13}C_1$ | | | 50% $^{13}C_1$ | | |
|---|---|---|---|---|---|---|---|---|---|---|---|---|
| m/z | $^{12}C$ | 10% $^{13}C_1$ | 50% $^{13}C_1$ | $^{12}C$ | 10% $^{13}C_1$ | 50% $^{13}C_1$ | $S_{L\_resid}$ | $S_{H\_cor}$ | L in (%) | $S_{L\_resid}$ | $S_{H\_cor}$ | L (%) |
| 319 m0 | 156460 | 153425 | 84507 | 66.6 | 60.2 | 33.2 | | | | | | |
| 320 m + 1 | 48250 | 63669 | 112421 | 20.6 | 25.0 | 44.2 | 18.6 | 6.4 | 9.6 | 10.2 | 33.9 | 50.5 |
| 321 m + 2 | 23579 | 28289 | 38071 | 10.0 | 11.1 | 15.0 | 9.1 | 2.0 | | 5.0 | 10.0 | |
| 322 m + 3 | 5038 | 7389 | 15467 | 2.1 | 2.9 | 6.1 | 1.9 | 1.0 | | 1.1 | 5.0 | |
| 323 m + 4 | 1199 | 1716 | 3268 | 0.5 | 0.7 | 1.3 | 0.5 | 0.2 | | 0.3 | 1.0 | |
| 324 m + 5 | 228 | 262 | 751 | 0.1 | 0.1 | 0.3 | 0.1 | 0.0 | | 0.0 | 0.2 | |
| Sum | 234754 | 254750 | 254485 | 100 | 100 | 100 | | | | | | |

Mathematical approaches to calculate stable isotope enrichment are already incorporated into existing software packages. Usually these approaches require the complete knowledge of the chemical composition of the analysed molecular fragment. Here we established a method to calculate stable isotope incorporation by subtracting natural occurring stable isotope abundances from experimentally derived mass spectra. This approach does not require prior knowledge of the chemical composition of the fragments and facilitating the analysis of stable isotope incorporation into unknown compounds. Furthermore, this strategy takes into account concentration-dependent changes of the mass isotopomer distributions, which are laborious to calculate. Starting from the MIF the total label incorporation is defined as the ratio of the intensity of the monitored heavy labeled mass fragment in the test sample ($S_H$) to the sum of the intensities of the heavy and light mass fragment ($S_L$). Unfortunately, this simple calculation could lead to an overestimation of label incorporation due to naturally occurring carbon, nitrogen and silicone isotopes in the compound and derivatization groups (FIG. 2c). The consideration of reference mass spectra provides the correction term for natural isotope abundance (Formula II.a) by multiplying the ratio of references naturally heavy mass fragment ($R_H$) to the light mass fragment ($R_L$) with the intensity of the light mass fragment in the sample ($S_L$) (Formula II.b) The corrected heavy intensity is then used to calculate the total label (Formula II). This calculation assumes the compounds to be labeled at a single position, which holds true for glycolytic intermediates after application of $^{13}C_6$-glucose. To calculate label incorporation into compounds labeled at multiple positions, as for instance TCA-cycle intermediates multiple correction steps are necessary. Alternatively, we employ a strategy to calculate the total label incorporation from the remaining intensity of the light fragment in the sample ($S_L$) (Formula I) which contains also the summed up information of the incorporated label at all positions. The amount of total label can be calculated from the amount of disappearing intensity of the light fragment ($S_L$) compared to light fragment in the reference ($R_L$).

We verified the calculation strategies by mixing known amounts of $^{13}C_1$-glucose with $^{12}C$-glucose and comparing the measured with the calculated isotope incorporation. The uncorrected strategy leads to an over-estimation of the label incorporation, as expected, due to the natural $^{13}C$, $^{29}Si$ and $^{30}Si$ abundance, and both correction strategies work precisely to calculate the correct amount of label (FIG. 2D and see Table 3).

TABLE 3

Validation of correcting strategies for the determination of isotope incorporation

| Expected iso- | $^{13}C$-abundance in glucose (%) | | |
|---|---|---|---|
| tope abundance (%) | Uncorrected | Targeted | Position-independent |
| 0 | 23.4 ± 0.09 | 0.0 ± 0.16 | 0.0 ± 0.12 |
| 1.98 | 24.7 ± 0.25 | 2.1 ± 0.42 | 2.0 ± 0.32 |
| 4.95 | 26.4 ± 0.21 | 5.0 ± 0.36 | 5.0 ± 0.27 |
| 9.90 | 29.6 ± 0.20 | 10.3 ± 0.33 | 10.1 ± 0.29 |
| 24.75 | 39.2 ± 0.79 | 25.3 ± 1.19 | 25.0 ± 1.26 |
| 49.50 | 56.8 ± 0.89 | 50.3 ± 1.18 | 49.8 ± 1.28 |
| 74.25 | 76.1 ± 0.78 | 74.2 ± 0.91 | 74.0 ± 0.94 |
| 89.10 | 89.0 ± 0.04 | 88.6 ± 0.04 | 88.4 ± 0.03 |
| 94.05 | 93.9 ± 0.14 | 93.8 ± 0.15 | 93.7 ± 0.15 |
| 97.02 | 96.8 ± 0.19 | 96.7 ± 0.19 | 96.7 ± 0.20 |
| 99.00 | 98.7 ± 0.04 | 98.7 ± 0.04 | 98.7 ± 0.05 |

$^{13}C_1$-Glucose (purity 99%) and unlabeled glucose were mixed in known ratios in three independent eplicates. Uncorrected values overestimate incorporation especially in the lower abundance range, whereas both calculation strategies (targeted which means labeling at single position and position-independent which means labeling at multiple positions) consider the natural $^{13}C$-contribution correctly.

Example 4

Application of pSIRM

Feeding cells with $^{13}C$-glucose allows monitoring of the activity of CCM, specifically of glycolysis and its branching points (FIG. 3A) at the level of [1] G6P into PPP and glycogen synthesis, [2, 3] DHAP/GAP into PPP and Glyc3P (lipid synthesis), [4] 3PGA into serine and glycine metabolism [5] and pyruvate into lactate, alanine or acetyl-CoA. We tested four different cell lines (HeLa, HEK293, T98G and HCT-116) at identical nutrient conditions fed with u-$^{13}C$- glucose for 3 minutes. Subsequently, the labeled fractions of metabolites (the product of peak intensity multiplied with percentage of label incorporation) were compared relative to T98G cells (FIG. 3b). Using this approach clear differences among the tested cell lines were observed. HeLa cells showed the highest glycolytic activity. $^{13}$C-isotope incorporation of fructose was detected in HeLa and HEK293 cells while $^{13}$C-labeled fructose-1-phosphate was detected only in HeLa cells. The time depended label incorporation in ribose-5-phosphate, an important intermediate of the pentose phosphate pathway, was comparable among all cell lines—nearly identical for G6P, DHAP, Pyr, Lac and Cit; only T98G cells displayed a different labeling pattern. HEK293 cells showed higher activity in amino-acid synthesis as the labeled fraction of alanine and serine were increased. These results clearly demonstrate the power of the presented method in order to highlight variations in carbon routing within different cellular systems.

Next we analysed the mode of action of two glycolytic inhibitors, 2DG and BrPyr. T98G cells were treated for 12 minutes with each inhibitor (2 mM), followed by 3 minutes of $^{13}$C-glucose incorporation in the presence of each inhibitor (FIG. 3c). BrPyr treatment reduced the labelled fraction of G6P and F6P whereas the total concentration of these compounds increased. The concentration of 3PGA diminished below the detection limit. Furthermore, downstream glycolysis was nearly completely inhibited: The carbon-flow into pyruvate, lactate and citrate was reduced by around 100%, verifying specific suppression of GAPDH activity. The alterations within glycolysis upstream may be explained by feedback inhibition of the hexokinase by the accumulation of hexose-phosphates. In comparison, the inhibitory effect of 2DG was negligible: 2 mM of 2DG reduced the amount of the $^{13}$C-fraction of hexose-phosphates by just 20% and affected only marginally isotope incorporation in pyruvate and lactate. Additionally, $^{13}$C-glucose incorporation into citrate extended after 2DG treatment (FIG. 3c). Increasing the 2DG concentration to 10 mM induced a stronger inhibition, but mainly due to an overall decline of metabolite pool rather than a decrease of $^{13}$C-label incorporation. With this data an inhibition of hexokinase-reaction, as proposed, can be excluded, because carbon-13 enters the lower glycolysis. However the overall metabolic activity seems to be affected under the influence of 2DG.

Furthermore the incorporation of $^{13}$C-Glucose downstream of G6P contradicts the proposed inhibition of the hexokinase-reaction by 2DG.

Discussion:

Isotope pulse labeling was the ultimate tool to unravel metabolic pathways in plants and animal cells. The further development of analytical techniques such as mass spectrometry and nuclear magnetic resonance allows quantitative and structurally resolved analyses of stable isotope incorporation, thereby enabling a time resolved analysis of known metabolic pathways, and potentially, the discovery of new connections within the metabolic network. Here we report the pSIRM workflow that integrates information about stable isotope incorporation and metabolomics analyses by introducing additional time-dependent information of the underlying pathway activities from a single measurement in a quantitative manner.

To achieve this goal we have improved the cell handling protocol, dealing with the need for removal of abundant compounds from cultivation medium, and optimized sample preparation and GC-MS measurements. The combination of improvements has created a highly reproducible analytical platform with a superior coverage of CCM. Using GC-TOF-MS technology offers further advantages: the quantification of compounds suffers less from matrix effects due to the strong electron impact ionization (EI), and thus external calibration could be applied for quantification of 45 compounds simultaneously. Additionally, the untargeted character of TOF-MS allowed for the measurement of carbon-13 incorporation in an unbiased manner.

The pSIRM approach follows the concept that dynamic labeling offers distinct advantages over steady-state label incorporation. Uniformly labeled $^{13}$C-substrates that would yield no information in stationary labeling can be used for dynamic labeling, making analysis both cheaper and more generally applicable. Using pSIRM we aimed at the comparison of different metabolic states rather than perfect numerical description of the underlying fluxes. The power of this concept was demonstrated by decoding the metabolic basis of synthetic lethality induced by metabolic inhibition of senescent lymphoma cells and in MYC driven cancer cells after ARK5 inhibition.

Finally, dynamic labeling allowed the measurement of short-termed changes within metabolism which cannot be monitored by long-term label incorporation experiments. The application of pSIRM in combination with metabolic inhibitors or toxins may resolve the position of the drug target within the metabolic network. This is illustrated by the inhibition of glycolysis by BrPyr and by the evident failure of 2DG to acutely block glycolysis. We observed an increased concentration of hexose phosphates after BrPyr treatment, indicating that hexokinase is not the major target of this inhibitor. Instead, a strong decline of carbon flow downstream of GAPDH clearly identifies this enzyme as the true target of BrPyr. By comparison, 2DG did not exhibit a primary target within glycolysis. 2 mM of 2DG reduced the $^{13}$C-labeled fraction of hexose phosphates by only 20%, and did not affect pyruvate or lactate levels, although a time- and concentration-dependent increase of 2-deoxyglucose-phosphate, resulting from phosphorylation of 2-deoxyglucose by hexokinase, was clearly detectable. Strikingly, cells adapted to 2DG treatment by increasing carbon flow into citrate (FIG. 3c). From these results, we surmise that the accumulation of 2-deoxyglucose-phosphate, which cannot be used in subsequent reactions, depletes the cellular phosphate pool by scavenging phosphate and, depending on the strength of depletion, impairing ADP re-phosphorylation and ATP dependent processes in the cell. At a very high concentration, here 10 mM, 2DG reduced the glycolytic flow up to 80%, however isotope incorporation rates in G6P were not affected.

In summary, the analysis of metabolic reprogramming after application of metabolic inhibitors in acute time scales will revolutionize metabolic research. The dissection of primary metabolic effects from secondary consequences is now possible. This will enable the evaluation of the direct impact of small molecules on metabolic pathways from metabolic changes provoked by transcriptional reprogramming. Thus, pSIRM has the potential to guide research into a new era of quantitative and time resolved understanding of metabolic regulation.

The invention claimed is:
1. A method for preparation of labeled metabolic products, comprising the steps:
  (a) providing a biological sample in vitro;
  (b) contacting the biological sample with a labeling buffer comprising a labeled substrate, wherein the substrate comprises at least one carbon atom and represents an educt or intermediate of a metabolic process of the biological sample and wherein the label is a stable isotope;

(c) washing the biological sample using a wash-buffer, wherein said wash-buffer comprises a carbon resource being a relevant nutrient resource of the biological sample such that the biological sample is precluded from carbon deficiency during said washing, wherein said carbon resource comprises the substrate according to step b), wherein said substrate in the wash-buffer may be labeled or unlabeled;

(d) quenching the biological sample such that metabolic processes within the biological sample are slowed down or stopped; and (e) extracting the labeled metabolic product from the biological sample.

2. The method according to claim 1, wherein the biological sample is a cell or tissue sample.

3. The method according to claim 1, wherein the labeled substrate is at least one of a peptide, an amino acid, a carbohydrate, a lipid, a fatty acid or pyruvate.

4. The method according to claim 1, wherein the stable isotope is at least one of $^{13}C$, $^{2}H$, $^{15}N$, $^{18}O$ or $^{34}S$.

5. The method according to claim 1, wherein the biological sample is contacted with the labeled substrate for <15 min.

6. The method according to claim 1, wherein the biological sample is contacted with the labeled substrate for 0.1 to 10 min.

7. The method according to claim 1, wherein the biological sample is contacted with the labeled substrate for 0.5 to 8 min.

8. The method according to claim 1, wherein the biological sample is contacted with the labeled substrate for 1 to 5 min.

9. The method according to claim 1, wherein the carbon source of the wash-buffer is at least one of a carbohydrate, a mono-or polyvalent alcohol, a fatty acid or an amino acid and/or combinations thereof.

10. The method according to claim 1, wherein the biological sample is quenched by cold treatment.

11. The method according to claim 1, wherein the labeled metabolic product is at least one of a carbohydrate, a (poly) peptide, a lipid, fatty acid, a nucleic acid or a metabolite.

12. A method for quantification of a labeled metabolic product from a biological sample, comprising the steps:

(a) Providing a test sample comprising a labeled metabolic product produced according to the method of claim 1;

(b) providing a reference sample comprising unlabeled metabolic product, preferably produced according to the method of claim 1, wherein the labeled substrate is replaced by unlabeled substrate;

(c) determining mass spectra of the test sample of step a) and of the reference sample of step b);

(d) calculating corresponding mass isotopomer fractions (MIF) for test and reference sample based on respective peak intensities or peak areas extracted from mass spectra of step c) and is calculated according to Formula 0:

$$MIF_x = \frac{Intensity_x}{\sum_{x=m0}^{x=m+n} Intensity_x} * 100\% \qquad (0)$$

wherein $MIF_x$=mass isotopomer fraction of the isotope on the position x in percent;

$intensity_x$=the measured peak intensity or peak area of the metabolic product on the position x;

$\sum_{x=m0}^{x=m+n} Intensity_x$=the sum of all peak intensities or peak areas in the predefined mass-range, from the unlabeled mass (M+0) to the complete labeled mass (M+n), which is defined by the maximum number of metabolically accessible atoms of the isotope to be analysed (n); and (e) quantifying the relative amount of labeled metabolic product in the test sample starting from the MIF calculated in step d), wherein:

relative amount of total labeled metabolic product is calculated according to Formula I:

$$L(\%) = \left(1 - \frac{S_L}{R_L}\right) \times 100; \qquad (I)$$

and relative amount of labeled metabolic product labeled at a single position is calculated according to Formulae (II), (II.a) and (II.b)

$$L(\%) = \frac{S_{H\_cor}}{S_{H\_cor} + S_L} \times 100 \qquad (II)$$

$$S_{H\_cor} = S_H - S_{L\_Resid} \qquad (II.a)$$

$$S_{L\_Resid} = \frac{R_H}{R_L} \times S_L \qquad (II.b)$$

wherein

L(%)=relative amount of labeled metabolic product in relation to total amount of metabolic product in the test sample;

$S_H$=measured relative amount (MIF) of test sample on anticipated heavy position;

$S_{H\_corr}$=calculated relative amount (MIF) of heavy mass fragment of test sample corrected for amount of naturally occurring stable isotopes;

$S_L$=measured relative amount (MIF) on light position of test sample;

$S_{L\_Resid}$=calculated relative amount (MIF) of naturally occurring heavy mass originating from light fragment on anticipated heavy position;

$R_H$=measured relative amount (MIF) of reference sample on anticipated heavy position;

$R_L$=measured relative amount (MIF) on light position of reference sample.

13. The method according to claim 12, wherein mass spectra in step c) are determined using at least one of mass spectrometry (MS), electron impact ionization (EI), electrospray ionization (ESI), atmospheric pressure chemical ionization (APCI), liquid chromatography (LC), gas chromatography (GC), or capillary electrophoresis (CE).

14. The method according to claim 12, comprising the step of analysing metabolic products in biological samples.

15. The method according to claim 12, comprising the step of analysing the effect of small molecules on metabolic processes.

* * * * *